(12) United States Patent
Moore

(10) Patent No.: US 11,474,998 B2
(45) Date of Patent: Oct. 18, 2022

(54) INTERACTIVE MEDICAL DATA QUERYING

(71) Applicant: 3D4Medical Limited, County Dublin (IE)

(72) Inventor: John Moore, County Dublin (IE)

(73) Assignee: 3D4Medical Limited, County Dublin (IE)

(*) Notice: Subject to any disclaimer, the term of this patent is extended or adjusted under 35 U.S.C. 154(b) by 425 days.

(21) Appl. No.: 16/638,425

(22) PCT Filed: Jul. 30, 2018

(86) PCT No.: PCT/EP2018/070610
§ 371 (c)(1),
(2) Date: Feb. 11, 2020

(87) PCT Pub. No.: WO2019/030043
PCT Pub. Date: Feb. 14, 2019

(65) Prior Publication Data
US 2020/0167351 A1 May 28, 2020

Related U.S. Application Data

(60) Provisional application No. 62/544,321, filed on Aug. 11, 2017.

(51) Int. Cl.
*G06F 16/33* (2019.01)
*G06F 16/242* (2019.01)
(Continued)

(52) U.S. Cl.
CPC ...... *G06F 16/2428* (2019.01); *G06F 16/8373* (2019.01); *G06T 17/005* (2013.01);
(Continued)

(58) Field of Classification Search
CPC ............. G06F 16/2428; G06F 16/2423; G06F 16/242; G06F 16/8373; G06F 16/835;
(Continued)

(56) References Cited

U.S. PATENT DOCUMENTS

2004/0083092 A1* 4/2004 Valles .................... G06F 40/30
704/9
2009/0030686 A1* 1/2009 Weng .................. G10L 15/1822
704/E15.001

FOREIGN PATENT DOCUMENTS

JP 4652504 B2 3/2011

* cited by examiner

*Primary Examiner* — Huyen X Vo
(74) *Attorney, Agent, or Firm* — Dinsmore & Shohl LLP

(57) ABSTRACT

A method of generating a digital audio-visual sequence comprising one or more three-dimensional structures and an audio stream in real time is disclosed, comprising the steps of capturing and processing vocal input from a user, identifying at least one semantic construct from the captured vocal input, matching identified semantic construct with at least one structure tag and at least one case tag, wherein the structure tag is associated with a three-dimensional structure and the case tag is associated with an alphanumerical description of the three-dimensional structure, and generating a sequence based on one or more matched structure tag(s) and one or more matched case tag(s). Generating comprises scheduling synchronous rendering of the three-dimensional structure in a user interface and voice synthesising of the alphanumerical description. An apparatus embodying the method is also disclosed, including display means for displaying the user interface, voice synthesising means for processing the alphanumerical description into an audio signal, and audio means for outputting the audio signal.

9 Claims, 7 Drawing Sheets

(51) Int. Cl.
*G06F 16/835* (2019.01)
*G06T 17/00* (2006.01)
*G06T 17/20* (2006.01)
*G10L 15/18* (2013.01)
*G10L 15/22* (2006.01)

(52) U.S. Cl.
CPC ........ *G06T 17/205* (2013.01); *G10L 15/1815* (2013.01); *G10L 15/22* (2013.01); *G10L 2015/223* (2013.01)

(58) Field of Classification Search
CPC ..... G06T 17/005; G06T 17/00; G06T 17/205; G06T 17/20; G10L 15/1815; G10L 15/18; G10L 2015/223; G10L 15/22; G16H 50/50; G16H 40/63
See application file for complete search history.

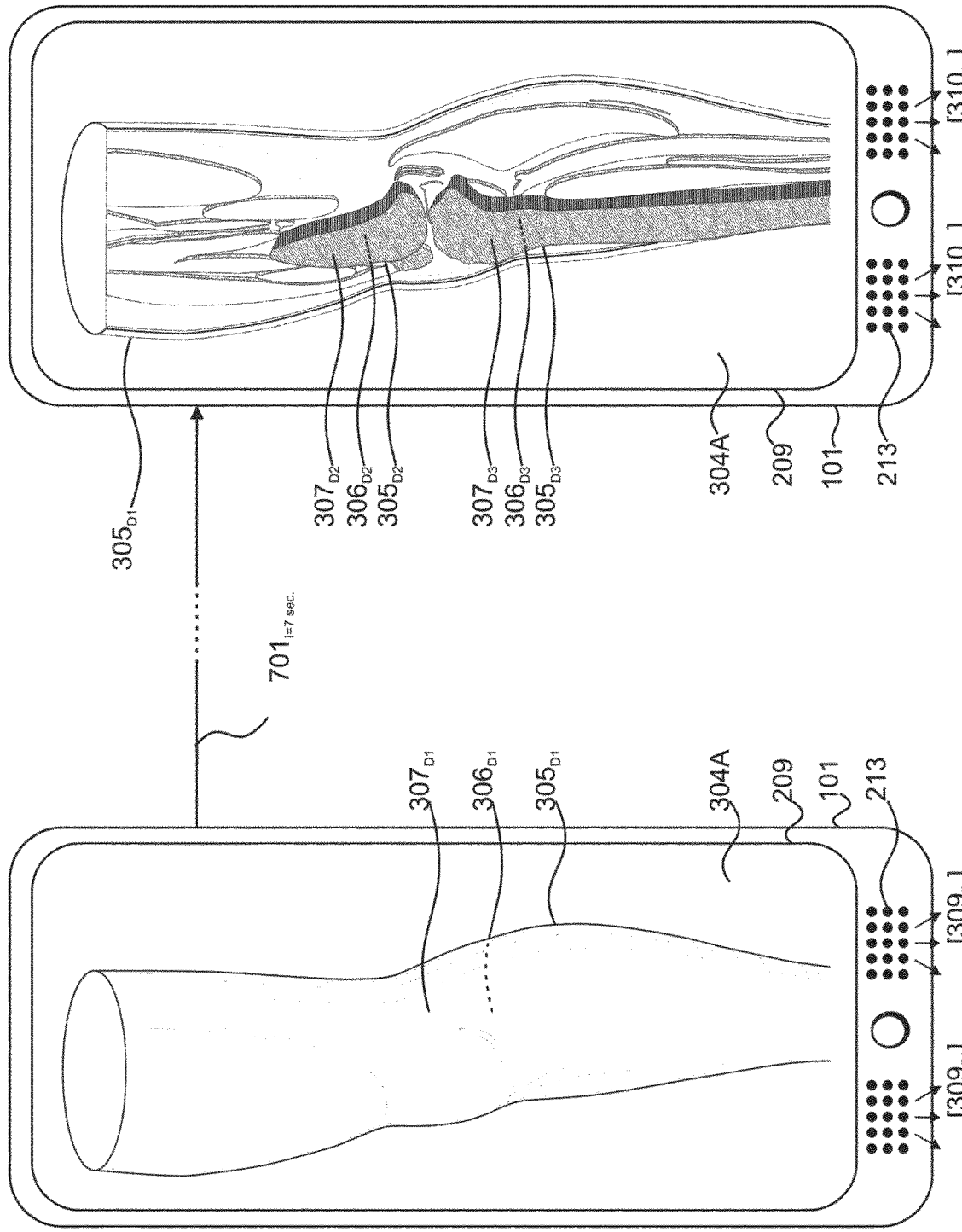

INTERACTIVE MEDICAL DATA QUERYING

CROSS REFERENCE TO RELATED APPLICATIONS

This application is a U.S. National Stage entry under 35 U.S.C. § 371 based on International Application No. PCT/EP2018/070610, filed on Jul. 30, 2018, which claims priority to U.S. Provisional Application No. 62/544,321, filed on Aug. 11, 2017. The embodiment of the priority applications are hereby incorporated herein in their entirety by reference.

FIELD OF THE INVENTION

The present invention relates to a method and apparatus for interacting with a medical data resource. More particularly, the present invention relates to a method and apparatus for voice interacting with a digital medical data source for obtaining three dimensional imagery and audio through a distributed software architecture.

BACKGROUND OF THE INVENTION

Many data processing techniques are known for outputting a three dimensional ('3D') structure, which is typically composed of one or more 3D polygon meshes and respective two-dimensional ('2D') texture maps, in a user interface on a display.

An example of a 3D structure is a computer rendering of the human body, with a first mesh defining the human skeleton having a respective texture with the appearance of bone material, a second mesh defining the human muscle architecture having a respective texture with the appearance of dark and deeply ribbed flesh, and a third mesh defining the human epidermis having a respective texture with the appearance of skin, wherein the relationships nest the first, second and third structures and respective textures within one another in a manner analogous with the real human body.

Selection of which 3D structure to process and output, and interaction with the one or more 3D structures output in the user interface, typically relies upon physical interaction between the user and an input device, such as a pointing device like a computing mouse, or a tactile interface if the display is touch-enabled.

The requirement to interact physically with an apparatus processing and displaying 3D imagery and/or outputting the descriptive narrative is a distinct disadvantage, particularly when a user, for instance a medical practitioner, needs to consult an anatomical plate during a procedure, wherein it may be cumbersome and time wasting to interrupt the procedure and follow hygiene requirements before interacting with the device and then before resuming the procedure, and wherein hands-free, vocal interaction would be highly preferential.

Moreover, in certain specialist environments like medical science and practice, it is frequently the case that imagery in a knowledge base, for instance anatomical imagery commonly referred to as 'plates', is accompanied by a detailed description of that imagery, commonly referred to as 'cases'. The narrative may be either generic, for standard anatomical features, or specific for known illnesses, injuries, ailments, procedures and the like about a specific anatomical feature, be it skeletal or an organ.

Whilst electronic repositories of cases are known, their consultation, i.e. the selection of which case to process and output, again typically relies upon physical interaction between the user and an input device, such as a pointing device like a computing mouse, or a tactile interface if the display is touch-enabled; then the reading of the selected case requires the user to focus upon a user interface on a display device, away from a task or procedure and so exhibiting substantially the same shortcomings as manipulating 3D plates.

The present invention aims to overcome or alleviate some or all of the above disadvantages, desirously in real time.

SUMMARY OF THE INVENTION

The present invention is a computer implemented method of capturing a vocal query into a script, reading that script, picking out key phrases in that script, and manipulating a 3D model to illustrate the key phrases in synchronicity, so that as the script is read and the 3D model is automatically shown, optionally with accompanying animation(s) such as zooming in or out panning tilting, removing or cutting model layers, highlighting aspects of a 3D model, and other manipulations. The method is implemented in a local or client-server software architecture delivering combined 3D and audio content upon a user's voice request.

According to a first aspect of the present invention, there is therefore provided an apparatus for generating a digital audio-visual sequence comprising one or more three-dimensional structures and an audio stream in real time. The apparatus comprises data storage means adapted to store the one or more digital three-dimensional structures, each associated with one or more structure tags; and one or more alphanumerical descriptions of the or each three-dimensional structure, each associated with one or more case tags. The apparatus also comprises data processing means adapted to capture and process vocal input from a user, to identify at least one semantic construct from the captured vocal input, to match identified semantic construct with at least one structure tag and at least one case tag, and to generate a sequence based on one or more matched structure tag(s) and one or more matched case tag(s), wherein generating comprises scheduling synchronous rendering of the three-dimensional structure in a user interface and voice synthesising of the alphanumerical description. The apparatus also comprises display means for displaying the user interface, voice synthesising means for processing the alphanumerical description into an audio signal, and audio means for outputting the audio signal.

According to a further aspect of the present invention, there is also provided a method of generating a digital audio-visual sequence comprising one or more three-dimensional structures and an audio stream in real time, comprising the steps of capturing and processing vocal input from a user, identifying at least one semantic construct from the captured vocal input, matching identified semantic construct with at least one structure tag and at least one case tag by applying a context identification algorithm comprising the steps of;

i) comparing the identified semantic construct against a tree of structure tags;

ii) identifying at least one structure tag that matches the identified semantic construct;

iii) applying a confidence value to the identified at least one structure tag, the confidence value describing the degree to which the at least one structure tag matches the identified semantic construct;

iv) where multiple structure tags are matched to the identified semantic contract, arranging the identified structure tags by confidence value; and v) selecting the structure tag having the highest confidence value relative to the other identified structure tags.

Wherein the structure tag is associated with a three-dimensional structure and the case tag is associated with an alphanumerical description of the three-dimensional structure, and generating a sequence based on one or more matched structure tag(s) and one or more matched case tag(s), wherein the step of generating further comprises scheduling synchronous rendering of the three-dimensional structure in a user interface and voice synthesizing of the alphanumerical description.

Suitably the tree of structure tags further comprises any from the group of at least a word index value, a command index value, a prefix length value, a value indicating the parent nodes and a value indicating the children nodes.

Preferably there are provided the further steps of applying a best view algorithm, the best view algorithm comprising the steps of: formalizing the identified semantic construct as a set of terms for processing, the set of terms for processing; assigning formal properties to the set of terms; estimating the rendering of the three-dimensional structure using the assigned formal properties against a set of rules; generating a list of formal operations describing the steps required to render the three-dimensional structure; executing the list of formal operations.

Advantageously the formal properties are selected from the group mathematical formal properties, contextual formal properties, and expert formal properties.

Suitably the set of rules include any from the group of building context data, mathematical analysis of the three-dimensional structure, and expert formal properties analysis.

Preferably the formal properties comprise contextual formal properties, wherein the contextual formal properties are determined by a set of contextual formal property rules.

Suitably the contextual formal property rules are selected from the group all valid, only specified, all valid intermixed, and all valid except specified.

According to yet another aspect of the present invention, there is also provided a computer program product recorded on a data carrying medium which, when processed by a data processing terminal, configures the terminal to capture and process vocal input from a user, identify at least one semantic construct from the captured vocal input, match identified semantic construct with at least one structure tag and at least one case tag, wherein the structure tag is associated with a three-dimensional structure and the case tag is associated with an alphanumerical description of the three-dimensional structure, and generate a sequence based on one or more matched structure tag(s) and one or more matched case tag(s), wherein generating further comprises scheduling synchronous rendering of the three-dimensional structure in a user interface and voice synthesising of the alphanumerical description.

Other aspects are as set out in the claims herein.

BRIEF DESCRIPTION OF THE DRAWINGS

For a better understanding of the invention and to show how the same may be carried into effect, there will now be described by way of example only, specific embodiments, methods and processes according to the present invention with reference to the accompanying drawings in which:

FIG. 7A is a graphical illustration of a first instance of the user interface of FIG. 3 during the data processing of FIGS. 4 to 6.

FIG. 7B is a graphical illustration of a second, later instance of the user interface of FIG. 3 during the data processing of FIGS. 4 to 6.

DETAILED DESCRIPTION OF THE EMBODIMENTS

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

The words "comprises/comprising" and the words "having/including" when used herein with reference to the present invention are used to specify the presence of stated features, integers, steps or components but does not preclude the presence or addition of one or more other features, integers, steps, components or groups thereof.

Figure 1:
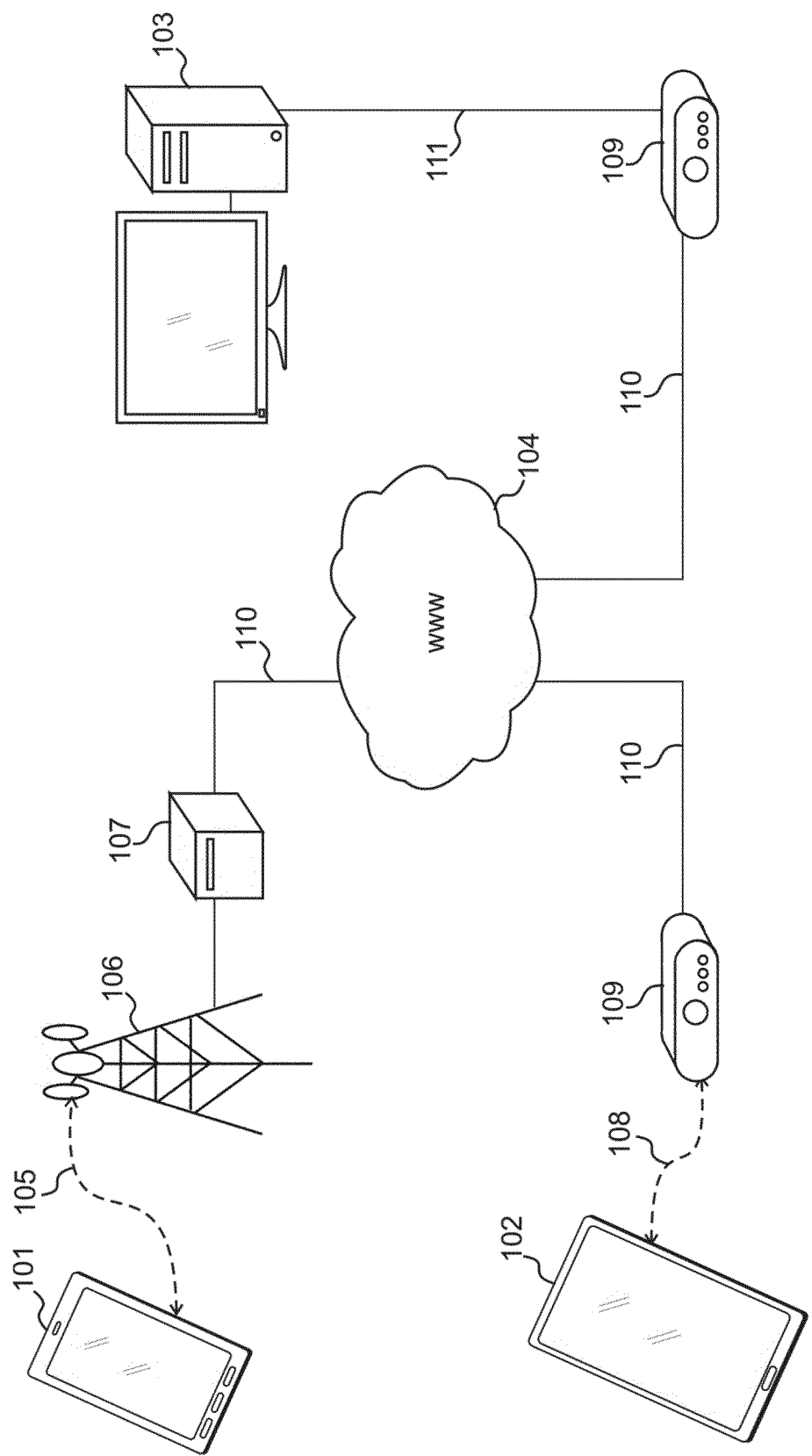
FIG. 1 shows a computing environment including a plurality of data processing terminals communicating data, including 3D structures and alphanumerical data, and a set of instructions according to an embodiment of the present invention.

Referring now to the figures and initially FIG. 1, there is shown a network environment in which several data processing terminals 101, 102, 103 are connected to one another over a Wide Area Network (WAN) 104, in the example the Internet.

Data processing terminal 101 is a mobile communication device which receives or emits data, including voice and/or text data, encoded as a digital signal over a wireless data transmission 105, wherein said signal is relayed respectively to or from the device 101 by the geographically-closest communication link relay 106 of a plurality thereof. The plurality of communication link relays $106_N$ allows digital signals to be routed between mobile devices 101 and their intended recipient by means of a remote gateway 107. Gateway 107 is for instance a communication network switch, which couples 110 digital signal traffic between wireless telecommunication networks, such as the network within which wireless data transmissions 105 take place, and the WAN 104. The gateway 107 further provides protocol conversion if required, for instance if the device 101 uses a Wireless Application Protocol ('WAP') or Secure Hypertext Transfer Protocol ('HTTPS') to communicate data.

Data processing terminal 102 is a mobile tablet—format device which receives or emits data encoded as a digital signal over a wireless data transmission 108, wherein said signal is related respectively to or from the computer 102 by a local wireless router 109 operating according to the IEEE 802.11 wireless transmission protocol ('WiFi'). The router 109 is itself connected to the WAN 104 via a conventional ADSL or optical fibre connection over a wired telecommunication network 110.

Data processing terminal 103 is a personal computer configured as a data server connected to the WAN 105 substantially as described in connection with device 102, however wherein a wired connection 111 to its respective router 109 is preferred to maximise data communication bandwidth.

In the environment of FIG. 1 therefore, the user of each terminal 101, 102 therefore has the use of a mobile communicating device configured to receive and communicate data encoded as a digital signal over a wireless data transmission, respectively from and to the server 103.

Figure 2:
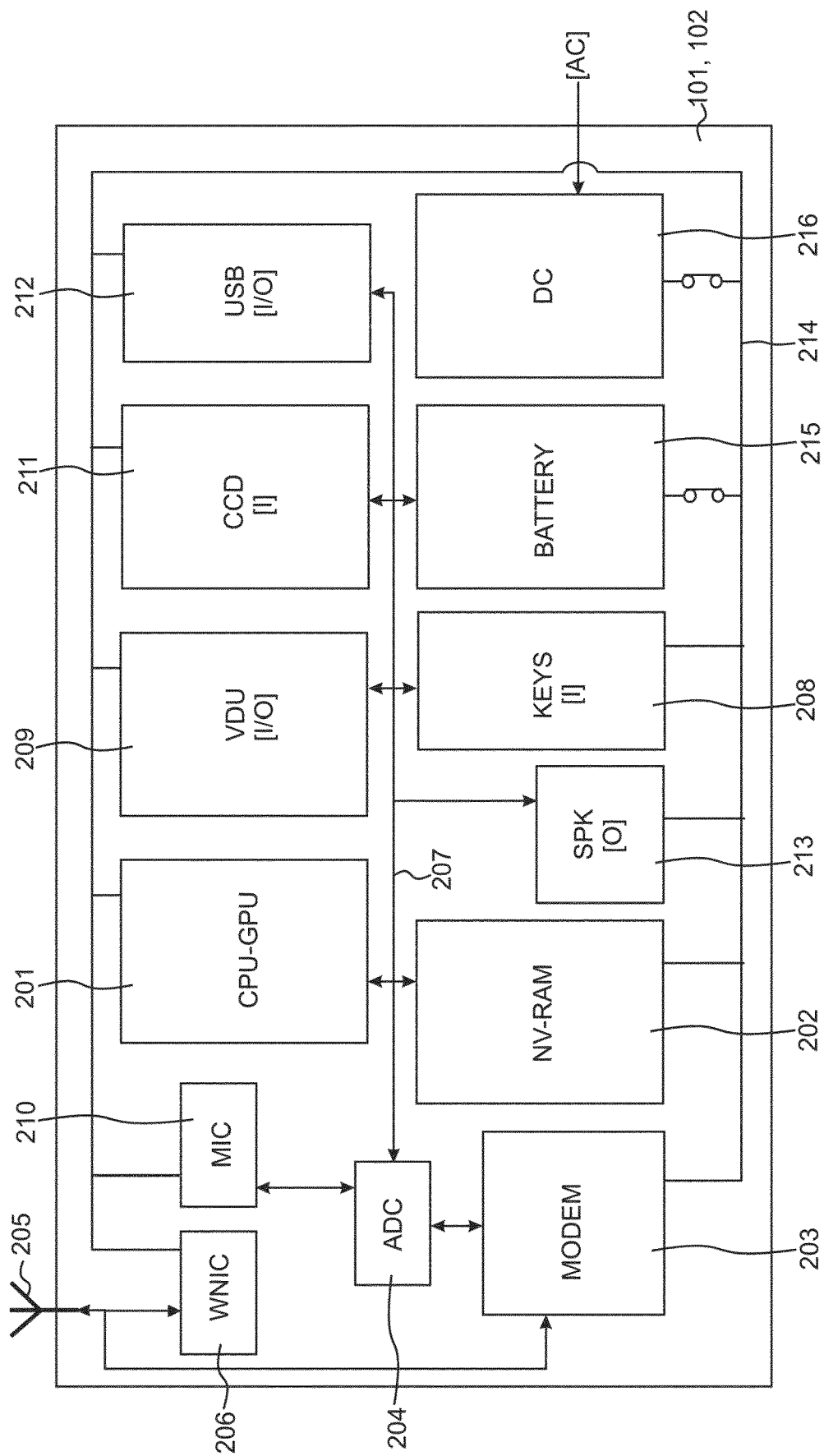
FIG. 2 illustrates a typical hardware structure of a terminal shown in FIG. 1.

A typical hardware architecture of either of the networking devices 101, 102 is shown in FIG. 2 in further detail, by way of non-limitative example. The mobile phone 101 and the tablet device 102 each include a data processing unit 201, for instance a general-purpose microprocessor, acting as the main controller of the data processing terminal and which is coupled with memory means 202, comprising volatile random-access memory (RAM), non-volatile random-access memory (NVRAM) or a combination thereof.

Each device further includes networking means. Communication functionality in mobile phone 101 is provided by a modem 203, which provides the interface to external communication systems, such as the GPRS, 3G or 4G cellular telephone network 106, 107 shown in FIG. 1, associated with or containing an analogue-to-digital converter 204, which receives an analogue waveform signal through an aerial 205 from the communication link relay 106 and processes same into digital data with the data processing unit 201 or a dedicated signal processing unit. Communication functionality in tablet device 102 is provided by a wireless network interface card (WNIC) 206 interfacing the tablet device 102 with the wireless local area network generated by router 109, and/or likewise by a 3G or 4G modem 203 as described above.

The CPU 201, NVRAM 202 and networking means 203 to 206 are connected by a data input/output bus 207, over which they communicate and to which further components of each device 101, 102 are similarly connected in order to provide wireless communication functionality and receive user interrupts, inputs and configuration data.

Accordingly, user input may be received from a data input interface 208, which for mobile phone 101 is a keypad with a limited number of multi-functional keys and/or a capacitive or resistive touch screen feature of the display unit 209 and, for tablet device 102, is a capacitive or resistive touch screen feature of the display unit 209.

Further input data may be received as analogue sound wave data by a microphone 210, digital image data by a digital camera lens 211 and digital data via a Universal Serial Bus (USB) 212. Processed data is output as one or both of display data output to the display unit 209 and audio data output to a speaker unit 213.

Power is supplied to the above components by the electrical circuit 214 of devices 101, 102, which is interfaced with an internal battery module 215, which itself may be recharged on an ad hoc basis by an electrical converter 216.

Figure 3:
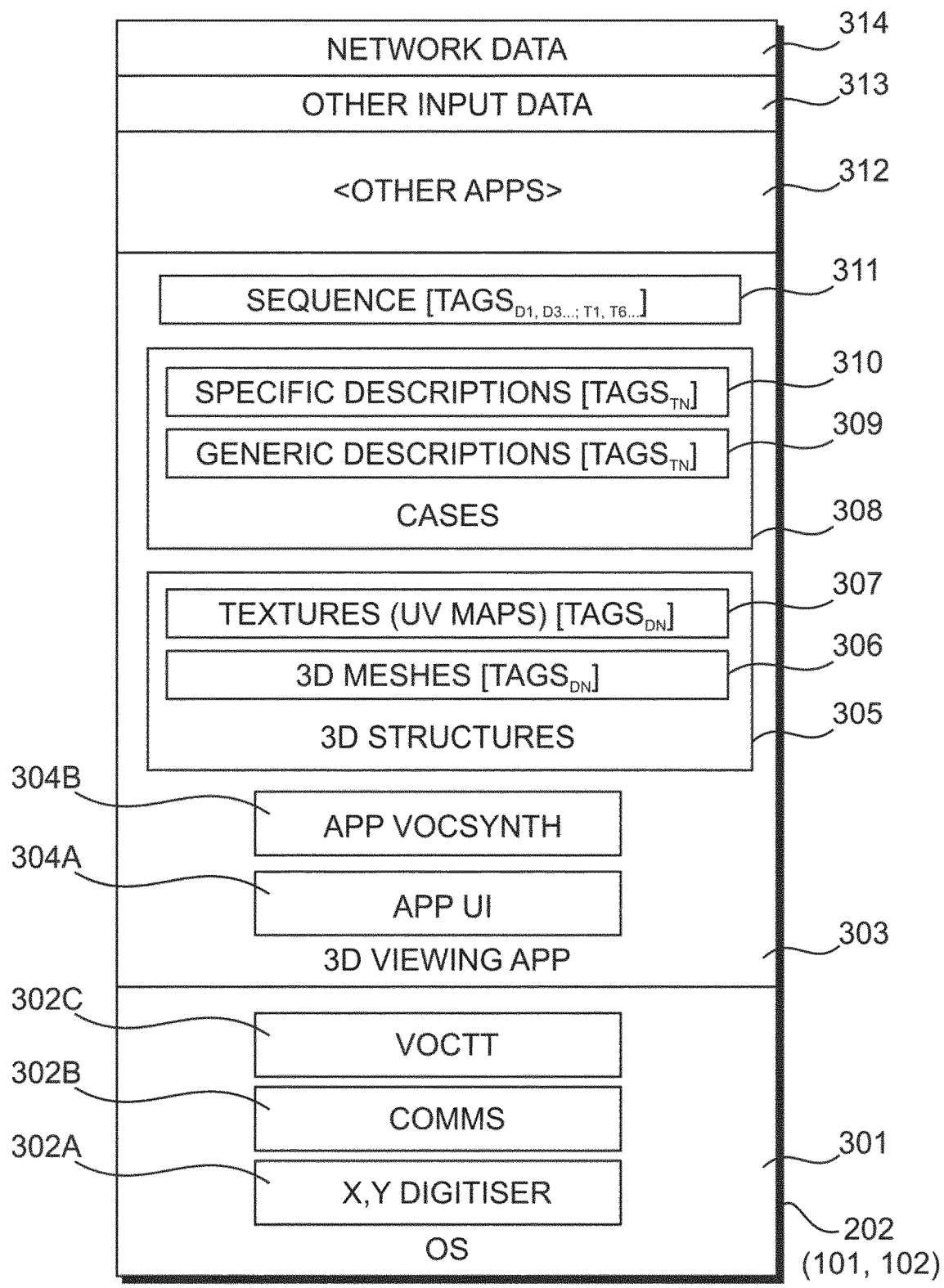
FIG. 3 illustrates the memory contents of a terminal of FIGS. 1 and 2, including the 3D structures, case data, sequence data and set of instructions at runtime, including a user interface.

FIG. 3 is a logical diagram of the contents of the memory means 202 of either data processing terminal 101, 102 at runtime, when configured to generate and output an audio-visual sequence in real time according to the present invention.

An operating system is shown at 301 which, if the device 101 is for instance an iPhone® mobile phone handset manufactured by Apple® Inc. of Sunnyvale, Calif., or if the device 102 is for instance an iPad® tablet computer likewise manufactured by Apple® Inc., is iOS® likewise distributed by Apple® Inc. The OS 301 includes digitiser subroutines 302A to read user input from the tactile display 209, communication subroutines 302B to configure the data processing terminal for bilateral network communication in the environment of FIG. 1 via the modem 203 and NIC 206, and a voice synthesiser module 302C for processing vocal input from the user digitised by the ADC 204 into machine-readable alphanumerical data.

Figure 4:
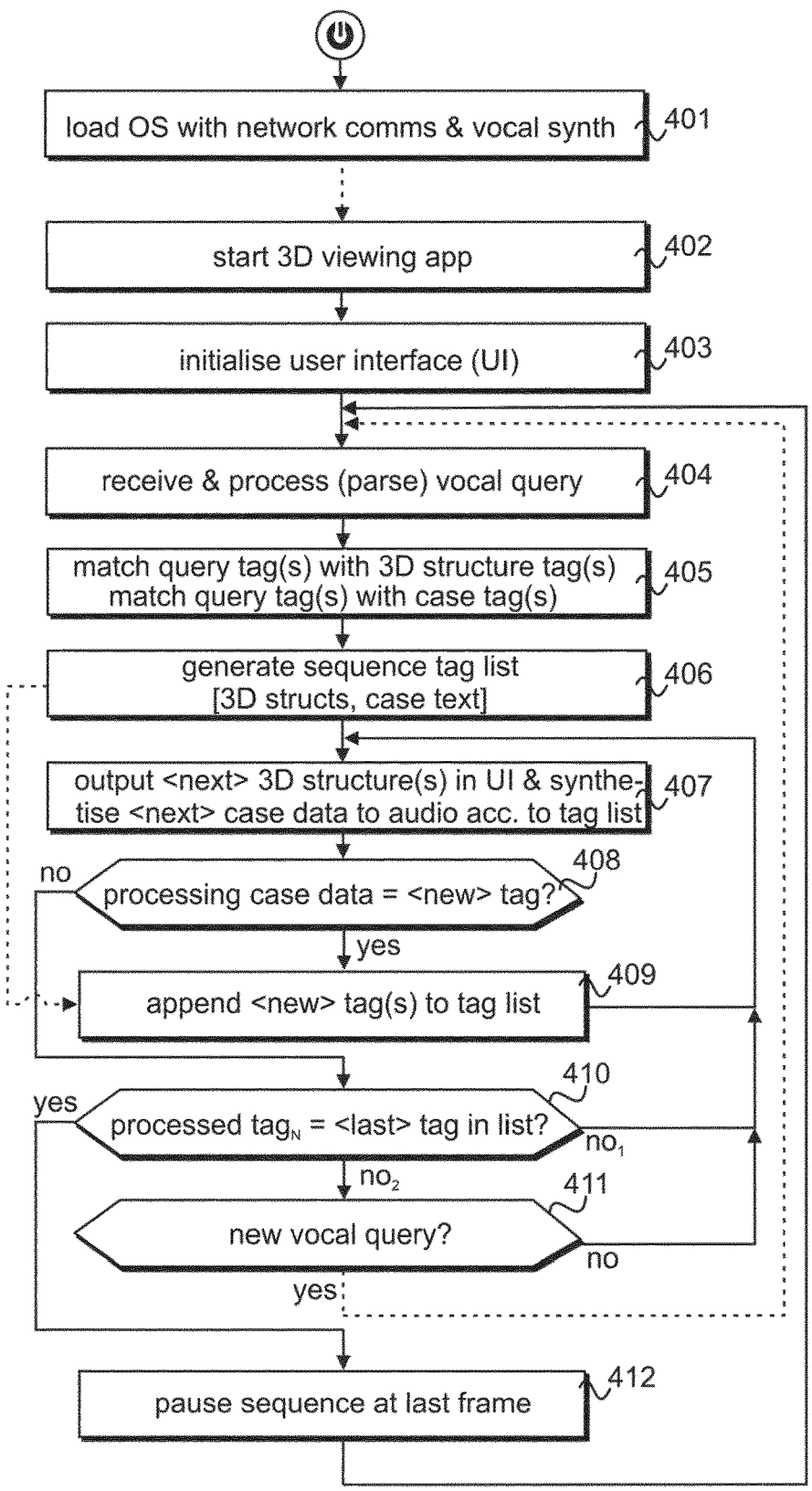
FIG. 4 details data processing steps performed by the terminal of FIGS. 1 to 3 for voice interacting with a digital medical data source and outputting a sequence of three dimensional and audio data according to an embodiment of the present invention.
Figure 5:
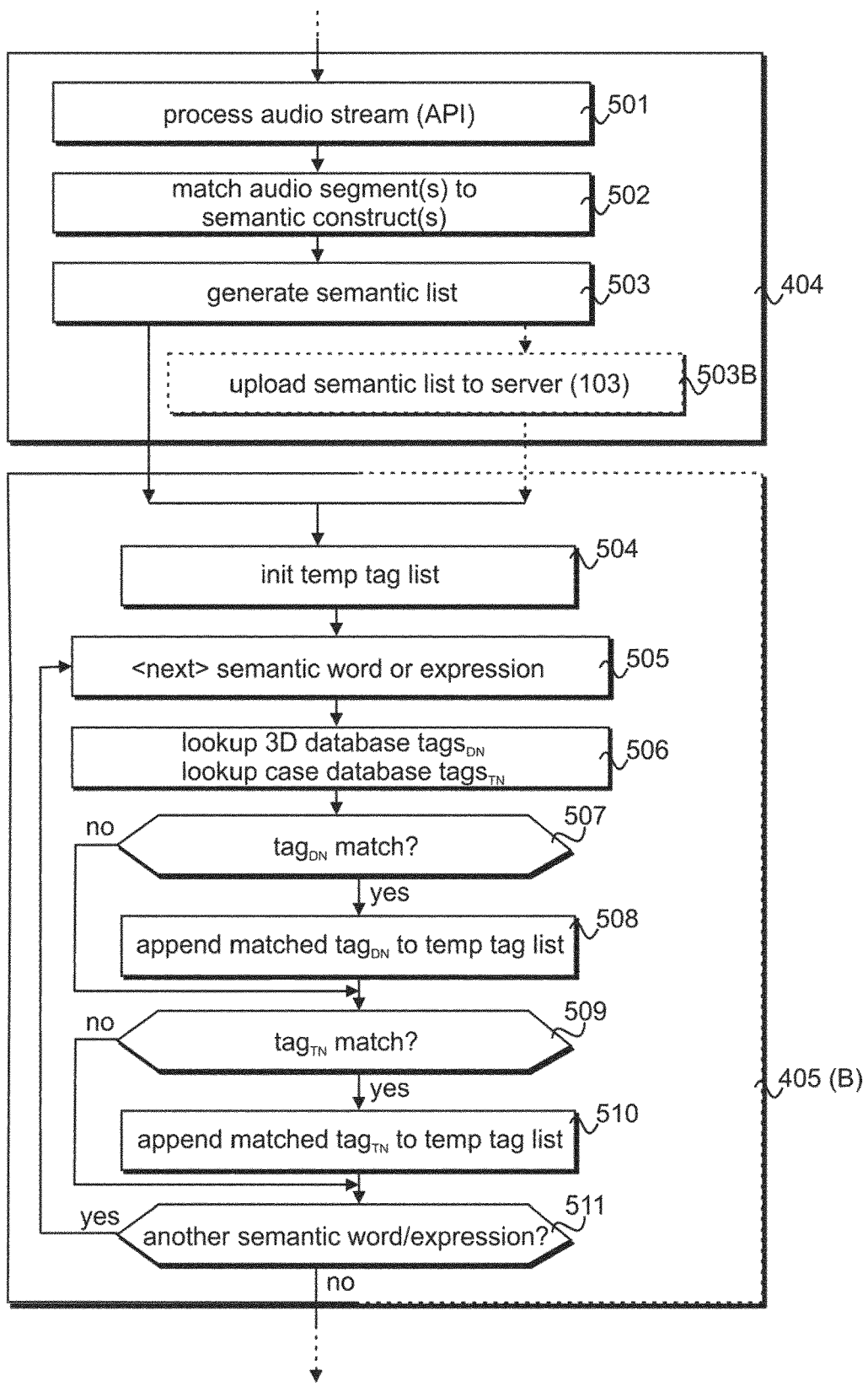
FIG. 5 further details data processing steps of parsing a vocal query and of matching tags in FIG. 4 according to an embodiment of the invention.
Figure 6:
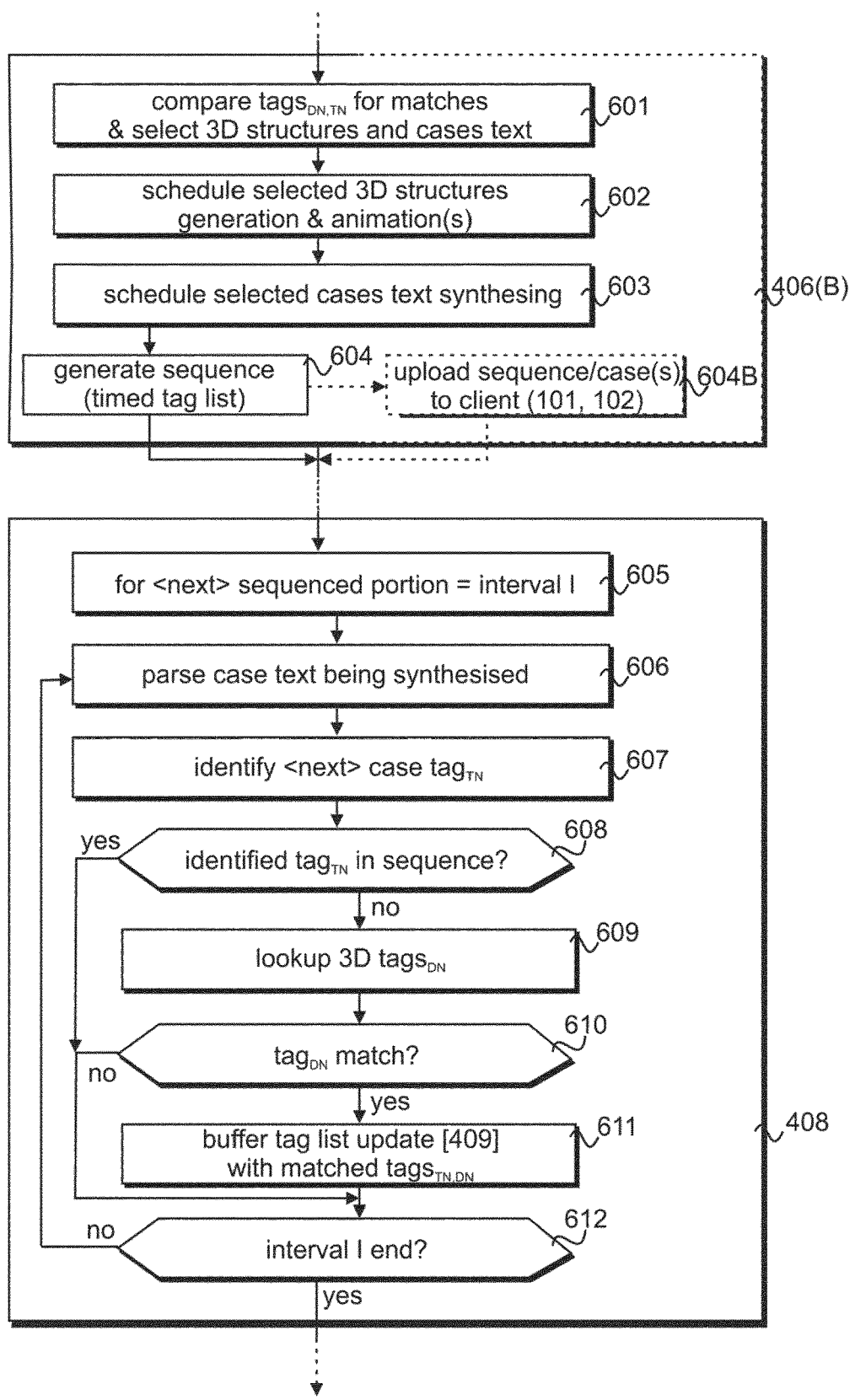
FIG. 6 further details data processing steps of generating a sequence as a tag list and of detecting new tags in FIG. 4 according to an embodiment of the invention.

An application is shown at 303, which configures the terminal 101, 102 to perform data processing steps described hereafter with reference to FIGS. 4 to 6, which embody a method of generating a digital audio-visual sequence comprising one or more three-dimensional structures and an audio stream in real time, in real time. The application 303 is interfaced with the OS 301, particularly subroutines 302C of the OS for capturing and processing user vocal input as sequence queries, but also subroutines 302A for reading and processing the two-dimensional user input to the touchscreen interface 209, and optionally also network communication subroutines 302B of the OS, via one or more suitable Application Programmer Interfaces.

An application user interface (UI) is shown at 304A, which the application 303 outputs to the VDU 209 and in which the application 303 both renders 3D structures 305 and reads two-dimensional X, Y user input effecting any selections therein on the touchscreen interface or digitizer via the relevant OS subroutine 302A. An audio synthesiser module is shown at 304B, through which the application 303 renders alphanumerical case data 308 as a human-intelligible audio signal and which the application 303 outputs through the device speakers 213.

3D structures 305 are created from at least one polygon mesh $306_N$, which is a collection of vertices, edges and faces and wherein faces usually consist of triangles (triangle mesh), quadrilaterals, or other simple convex polygons, and one or more UV texture maps $307_N$, which are two-dimensional images applied to faces of the 3D structures $306_N$ when rendering the structure 305. Structures 305 may also be layered, as consisting of nested 3D structures $306_N$ each having a same or respective UV texture map $307_N$, associated with its respective faces.

Each individual structure 305 and its component mesh(es) and texture(s) are referenced in the application 303 by at least one or more logical $tags_{DN}$. For instance, each of the mesh 306 and the skin texture 307 associated with a structure 305 corresponding to a whole human right leg, may be referenced with at least the tag "right leg", abbreviated '$_{D1}$' in the present description and figures for the sake of not obscuring the description unnecessarily. It will be readily understood from the foregoing, that implementations of the inventive concept may achieve improved granularity with additional and more discrete tags, for instance each of the mesh 306 and the skin texture 307 associated with a structure 305 corresponding to a whole human right leg, may be additionally referenced with the tags "human", "body", "lower limb", "leg", "right".

Cases shown at 308 comprise generic descriptions 309 of 3D structures 305 in alphanumerical form, substantially structure-respective discrete text files, either created at the server 103 from an anatomical knowledge base, or generated in real time from the 3D structure tags$_{DN}$ identified when processing a user vocal query, subject to the memory capacity of the user apparatus 101, 102, the amount and granularity of stored 3D structure tags$_{DN}$ and the processing capacity of the user apparatus 101, 102. Cases 308 may also comprise specific descriptions 310 of illnesses, ailments, injuries, procedures and similar ancillary information about each 3D structure 305, again in alphanumerical form, substantially structure-respective discrete text files, and again either created at the server 103 from an anatomical or medical knowledge base, or generated in real time from the 3D structure tags$_{DN}$ identified when processing a user vocal query.

As is the case for 3D structures 305, each individual generic or specific case 309, 310 is referenced in the application 303 by at least one or more logical tags$_{TN}$. For instance, the description of a whole human right leg may be referenced with at least the tag "right leg", abbreviated '$_{T1}$' in the present description and figures for the sake of not obscuring the description unnecessarily. It will be readily understood from the foregoing, that implementations of the inventive concept may achieve improved granularity with additional and more discrete tags, for instance the description of a whole human right leg, may be additionally referenced with the tags "human", "body", "lower limb", "leg", "right". Following from this example, and with reference to the later description of FIGS. 7A and 7B herein, the description of the femur within a human leg, may be referenced with the tags "leg", "skeleton" and "femur", abbreviated '$_{T2}$' and the description of the tibia within a human leg, may be referenced with the tags "leg", "skeleton" and "tibia", abbreviated '$_{T3}$' in the present description and figures for the sake of not obscuring the description unnecessarily.

A sequence file is next shown at 310 which, as will be made clear from the description of FIGS. 4 to 6 herein, comprises a list of 3D structure and case tags$_{DN,TN}$ embodying an audio-visual sequence generated in response to receiving and processing a user vocal query.

Further local data 313 and network data 314 may be stored in the memory means 202 of the data processing terminal 101, 102 at runtime, some or all of which may be processed either by the application 303 or by or for another application 312 being processed in parallel with application 303. An example of further local data is for instance local user input 311 read by the OS 301 in real time from the hardware interface 209, but which user input lies outside the user interface 304 of the application 303. An example of further network data is for instance remote application updating data 314 communicated by the remote server 103 over the WAN 104.

With reference to FIGS. 4 to 6 now, after powering up the apparatus 101, 102 and optionally accessing and downloading the 3D viewing application 303 from the remote server 103 across the network described in FIG. 1, the 3D viewing application 303 is started locally at step 402 and the user interface 304 is instantiated on the VDU 209 at step 403 as a result.

A user of the apparatus 101, 102 may then input a vocal query to the apparatus through the microphone 210 which the ADC 204 processes into digital speech data and which the voice-to-text module 302C of the OS 301 processes into alphanumerical data. At step 404, the application 303 processes the alphanumerical query to extract semantic words or expressions, which are subsequently compared with alphanumerical entries corresponding to tags of 3D structures 305 and cases 308 at step 405.

A context identification algorithm is then used to determine the sequence of actions to be performed by the software from the processed alphanumerical query (i.e. on the semantic words and/or expressions subsequently compared with alphanumerical entries corresponding to tags of 3D structures 305 and cases 308 at step 405).

The context identification algorithm uses a search tree to determine the actions required from the alphanumerical query. The algorithm applies a confidence value to the processed alphanumerical query and take a guess at the most appropriate branch of the search tree to use in order to provide the most appropriate result.

The context identification algorithm takes the processed alphanumerical query and converts it into an array of word indices. These are then recursively searched through the search tree. All commands that produce a match are gathered and a confidence value applied to each. The commands are then sorted by confidence value, i.e. those which the algorithm is most confident is the requested demand first. The algorithm then outputs those commands with the greater confidence value.

Confidence values are determined by comparing the number of words in a Recognised Command against the words of an array of word indices in the Target Input Phrase. For example, if an array of word indices is "Please show me the skin and the fat", and a potential command at a node of the decision tree is "show skin fat", a confidence value of 3/8 is assigned "show skin fat" is recognised with a confidence value equal to 3/8. If a further recognised command at a node is "show skin" only, then that node would be assigned a confidence value of 2/8 (i.e. a lower confidence value as that node is less relevant as it shows the skin only and not the fat as requested in the array of word indices).

By way of example, each node of the search tree comprises a word index value, a command index value, a prefix length value, a value indicating the parent nodes and a value indicating the children nodes relative to the node in question. The command index value has two components, a payload and a prefix. Prefixes detail an action to be carried out, such as show, add, remove, etc. Payloads detail the object to which the command is to be carried out on, such as skin, fat, or any other object that the software is capable of displaying. The search tree may be exported as a binary file.

At step 406, an audio video sequence comprising 3D structure and case text is generated on the basis of matches output by step 405, as a tag list. At step 407, the viewing application 303 fetches, renders and outputs one or more 3D structures 305 in the application UI 304A and the synthesiser module 304B thereof outputs the alphanumerical case data 309, 310, 311 through the apparatus speaker 213.

In order to ensure that the content displayed to the use is presented in the best way (i.e. such that no adjustment of the content is required in order to obtain a more preferably view by a use), a best view algorithm is used. The best view algorithm optimises the way the 3D structure is exposed on a display.

The best view algorithm negates the need for a human to manually determine the best view of a 3D structure to be presented to an end user. The algorithm uses mathematical, contextual, and expert criteria to determine the optimum way to present a 3D structure on a display to an end user.

Once the 3D structure to be displayed has been determined by the context identification algorithm, the 3D structure is formalised as a set of terms for processing by the best view algorithm. The set of terms comprise data (formal properties).

There are the following kinds of formal properties that the set of terms can be assigned.

Mathematical formal properties which include the dimensions of the 3D structure or surrounding structures, volume, centre of mass, prevailing direction of the 3D structure (e.g. horizontal or vertical), and shaping curve points set for the main planes of orientation.

Contextual formal properties include details regarding the context the 3D structure is in. This includes a subset of other objects from sets of terms from 3D structures adjacent to the 3D structure under consideration. The subset of other objects from sets of terms from adjacent 3D structures only includes information relating to the aspects of the adjacent 3D structures that must be displayed with the 3D structure under consideration. All other data relating to the adjacent 3D structures is omitted.

Expert formal properties include definitions of 3D structures defining that 3D structure as belonging to a particular category, such as skin, or bone etc . . . Expert formal properties may include additional extra context such as a set of other objects from the set of terms that are not a part of the considered 3D structure, but according to the expert, must also be displayed with the 3D structure in consideration. Such Expert formal properties can ensure that the displayed 3D structure makes sense in context or that the 3D structure can be articulated relative to other adjacent 3D structures in a life-like manner.

Expert formal properties can further include post processing information such as that detailing extra operations on a considered 3D structure which can improve the presentation of that structure (such operations include cut, pen, label, and highlight).

Once the set of terms has been equipped with the formal properties the 3D structures for display (or parts thereof if an adjacent 3D structure) are identified by its structure tag. The system running the best view algorithm then imports the set of terms and formal properties associated with that 3D structure and produces estimates of how to display the 3D structure against a set of rules.

Depending on the strength of the estimate the best view algorithm takes decisions and generates a list of the formal operations which need to be executed in order to display the 3D structure in the optimum way. The formal operations are then executed by the system to display the 3D structure in the optimum way.

In the best view algorithm, after identifying the object to expose, the system running algorithm gets a set of properties for the object and estimates them against the criteria and rules of exposure shaping the sequence of operations that are being conducted which will result in the best view for this particular object.

The estimation process depends on the number and the values of the formal properties which an object has. Properties would have the priorities to rank their influence. Expert properties will prevail on top of Contextual properties which will prevail on top of Maths properties. Each of them would have ranks within their respective types. Orientation would prevail on top of the Mass Centre. The algorithm conducts analysis on top of the priorities and applies the rules of shaping the list of operations. Rules are part of algorithm code and cannot be specified at this stage, they may vary.

The estimates are generated from a priority value assigned to each of the formal properties, i.e. the formal properties are ranked by a priority value. By way of example, the Expert formal properties prevail over the Contextual formal properties, which prevail over the Mathematical formal properties. Within each formal properties specific values also contribute to the determination of the priority value, for example, within the Contextual formal property, the orientation would prevail over the mass centre of that object, therefore orientation would be assigned a higher priority value than the mass centre.

The rules used by the best view algorithm against which the estimates are compared are applied sequentially against the set of terms in order to determine the operations needed to present the 3D structure in its best view.

The rules include building context data that identifies 3D structure context and construction according to the contextual formal properties and the expert formal properties.

The rules further include mathematical analysis of the 3D structure to be displayed and surrounding 3D structures to ensure visibility of the 3D structure to be displayed. This determines the position, angle of rotation, and magnification level the 3D structure to be displayed is presented in and to maximise the visible volume of that 3D structure on the display.

The rules also comprise details of how to analyse the Expert formal properties to determine whether post processing is required.

Once the best view algorithm has determined a the list of mathematical, contextual, and expert criteria to be used and processed these via the rules, the resulting list of conditions are sorted as a list of necessary operations to be applied to the 3D structure to be displayed in order to present it optimally to the user.

The Contextual formal properties defines connections between the 3D structure to be displayed and surrounding 3D structures that may be immediately adjacent or would otherwise obscure the 3D structure to be displayed (e.g. skin that covers a muscle that a user wishes to view). Surrounding 3D structures can include incidental data such as text and media too. The defined connections are determined using a set of contextual formal property rules to determine the actions needed to apply to the 3D structures for present the 3D structure to be displayed in a sensible context.

The connections are mapped to the 3D structures and as such comprise a text prefix detailing the context for a command object. The connections further comprise command objects which defines the relationship between the context of a given 3D structure, that 3D structure, and the operation to be conducted on that 3D structure in that given context.

The connections can also comprise any other necessary data such as 3D models, text, and media to be displayed with a given 3D structure in a given context.

The connections are processed via a set of contextual formal property rules. Such contextual formal property rules determine the most appropriate context to apply and include the following.

"All valid"—all text prefixes are added and used to make contextual strings consisting of each text prefix and 3D Structure to which it is to be applied.

"Only specified"—only those text prefixes that are defined by the respective contextual formal property rule is applied.

"All valid intermixed"—all text prefixes are added and then combined to produce a new array of text prefixes.

"All valid except specified"—only those prefixes that are not defined by the respective contextual formal property rule are applied.

A question is next asked at step 408 about whether the alphanumerical case data processed by the synthesiser module 304B comprises a new tag not previously included in the tag list output at step 406. If the question at step 408 is answered positively, then the new tag is appended to the existing tag list for expanding the audio visual sequence currently being output by the viewing application 303, wherein control returns to step 407. Alternatively, if the question of step 408 is answered negatively, then a next question is asked at step 410, about whether the tag currently being processed in the tag list is the last tag in that list. If the question of step 410 is answered negatively, control again returns to step 407 and the viewing application 303 continues to output the 3D structure(s) 305 in the UI 304A and to synthesise the alphanumerical case data output through the speaker 213.

Further, and in parallel a last question is asked at step 411, about whether the viewing application has received additional vocal query data from the user whilst the audio visual sequence is being output, for instance a further query about a discreet aspect of the 3D structure shown in the UI 304A or a request for alternative case data about that structure, such as an ailment or illness. If the question of step 411 is answered negatively, control again returns to step 407. Alternatively, when the question of step 411 is answered positively control returns to step 404, for the new vocal query to be processed, the semantic word or expressions thereof to be matched against database tag(s) and a new audio visual sequence to be generated, according to steps 404-406, which is subsequently appended to the existing tag list at step 409, in substantially the same manner as when the application detects new tags from the alphanumerical case data at the question of step 408. The processing of such interrupting vocal queries detected at the question of step 411 is shown in dotted lines in FIG. 4 to denote that this processing takes place whilst the sub-processing loop of steps 407-409 continues on the basis of the original tag list last output by step 406.

Alternatively, the question of step 410 is answered positively and, when the last tag in the list has been processed, the viewing application 303 pauses the audio visual sequence at its last frame at step 412 in the UI 304A, then awaits a new vocal query from the user by returning control to step 404.

The vocal query processing step 404 is further detailed in FIG. 5, wherein the digital audio stream processed by the voice-to-text module 302C and passed to the viewing application 303 through an application-programmer interface (API) is shown at step 501. Audio segment(s) in the digital audio stream are matched to one of more semantic construct(s) at step 502, wherein semantic construct(s) are alphanumerical expressions constituting words including names, adjectives, numbers, adverbs, verbs and more. At step 503, the viewing application generates a semantic list based on the matched semantic construct(s), consisting of words, adjectives and/or numbers but excluding redundant semantic construct(s) such as connectives and adverbs.

The present invention is capable of embodiment either as a standalone application 303 obtained from the server 103, wherein steps 402-412 may all be processed at the user apparatus 101, 102; or as a distributed method wherein at least some of steps 404-411 (but excluding at least step 407, which is local to the user apparatus 101, 102 in either case) may be processed at the server 103, for instance to relieve the user apparatus CPU 201 of the processing burden. Accordingly, in FIGS. 5 and 6, both embodiments are shown, wherein method steps illustrated in dotted line, fully or partially, correspond to the second embodiment involving data processing at the server 103.

Reverting now to the description of FIG. 5, the semantic list generated at step 503 may thus be uploaded by the user apparatus 101, 102 to the server 103 at a step 503B, for the server 103 to next process step 405, which is further described hereafter. In the alternative embodiment wherein all processing is carried out at the user apparatus 101, 102, step 405 begins by initiating a temporary tag list at step 504. The first or next semantic word or expression in the list of step 503 (503B) is selected at step 505 and the database of 3D structure tags$_{DN}$ and case tags$_{TN}$ is looked up at step 506 for a corresponding entry.

A first question is accordingly asked at step 507 about whether a 3D structure tag$_{DN}$ has been matched to the current semantic word. If the question of step 507 is answered positively, then the matched 3D structure tag$_{DN}$ is appended to the temporary tag list of step 504 at step 508. Alternatively, if the question of step 507 is answered negatively, or after the appending of step 508, a next question is asked at step 509 about whether a case tag$_{TN}$ has been matched to the current semantic word. If the question of step 509 is answered positively, then the matched case tag$_{TN}$ is also appended to the temporary tag list of step 504 at step 510.

Alternatively, if the question of step 509 is answered negatively, or after the appending of step 510, a final question is asked at step 511, about whether there remains another semantic word or expression in the semantic list to consider. If the question of step 511 is answered positively, control returns to step 505 for selecting the next semantic word or expression in the list and forming the matching and appending of steps 506-510. Alternatively, and eventually, the question of step 511 is answered negatively, whereby all 3D structure and case tags$_{DN,TN}$ have been identified and appended in the tag list such that the sequence may now be generated at step 406, which is further described with reference to FIG. 6.

Step 406 begins by comparing the tags$_{DN,TN}$ listed in the temporary list against the 3D structures 305 and cases 308 at step 601. Parameters may be input by way of defaults or by the user for the generation of sequences such as zooming, panning, and tilting of 3D structures in the user interface during output at step 407, likewise the speed at which the synthesiser module 304B outputs, i.e. reads out, the case text. At step 602 therefore, the application schedules the generation and any required animation(s) of the 3D structures selected at step 601 and, at step 603, the animation likewise schedules the synthesising of the case(s) text selected at step 601. The application then generates the sequence at step 604 as a timed tag list 311. In the embodiment wherein processing is distributed to the server 103, the server 103 uploads the sequence generated at step 604 to the client device 101, 102 at an additional step 604B. The local viewing application 303 subsequently outputs the 3D structures and synthesises the case at step 407 according to the generated sequence of step 604 (604B).

The logic of the question 408 is also further described in FIG. 6 and begins by declaring a time interval I at step 605 corresponding to the duration of the next sequenced portion of the sequence being processed, for instance corresponding to the rendering and optional zooming, panning and/or tilting of a 3D structure which is time-bounded by the duration of the synthesising of the case text corresponding to that 3D structure. At step 606, the viewing application 303 parses the case text being synthesised and identifies a semantic word which it compares against stored case tags$_{TN}$ at step 607 for identifying a matching case tag$_{TN}$.

A question is then asked at step 608 about whether the identified tags$_{TN}$ is already present in the timed tag list of step 604 at step 608. If the question of step 608 is answered negatively, then a second attempt is made at step 609, to match the identified case tags$_{TN}$ with a corresponding 3D structure tag$_{DN}$ at step 609.

A question is thus asked at step 610, about whether a match has been established with a 3D structure tag$_{DN}$ if the question of step 610 is answered positively, then the application has identified new case data 309, 310 and a 3D structure 305 which are not included in the current sequence (timed tag list) and the identified tags$_{DN,TN}$ are buffered as an update to the timed tag list for appending at step 409.

Alternatively, if the question of 608 is answered positively (signifying that the identified case tag$_{TN}$ is already in the sequence) or the question of 610 is answered negatively (signifying that the new case data has no 3D structure counterpart), control proceeds to a last question at step 612, likewise immediately after the buffering of step 611, about whether the time interval I initially declared at step 605 is expired.

If the question of step 612 is answered negatively, control returns to step 606 for identifying a next case tag$_{TN}$ in the case text being synthesised and so on and so forth. The question of step 612 is eventually answered positively such that control proceeds to step 409 for appending the matched additional 3D structure and case tags$_{DN,TN}$ to the sequence/timed tag list at step 409.

FIGS. 7A and 7B illustrate respective outputs over time of the viewing application 303 embodying the method according to the embodiment of FIGS. 4 to 6. In the example of these Figures, a sequence 311 has been generated by the user asking aloud "what is the tibia?". The sequence 311 generated according to the invention comprises structure tags$_{DN}$ and case tags$_{TN}$ representative of the leg's main structure, and sub-structures nested within, corresponding to skeletal and muscle features, including inter alia the tibia bone. The sequence is generated with a list of tags starting with the generic representation 305$_{D1}$ and description 309$_{T1}$ of a leg as shown in FIG. 7A and the synthesising of the generic leg description 309 $_{T1}$ is determined to require seven seconds (shown at 701).

Initially at FIG. 7A, the user interface 304A therefore displays a human leg as a rendered three dimensional structure 305 D1 composed of the mesh 306 D1 covered with a skin texture 307 D1, which may be animated with zoom and/or rotating and/or translation effects or not, whilst the corresponding case comprising the generic description 309 $_{T1}$ is synthesised and output by the speaker array 213 of the user apparatus 101. As the synthesizing of the generic description 309 $_{T1}$ ends, the mesh 306$_{D1}$ and texture 307$_{D1}$ of the leg are cut away transversally and the various sub-structures 305$_{DN+1}$ and their respective textures 307$_{DN+1}$ corresponding to the internal anatomy of a leg are rendered into the UI 304A, including inter alia the 3D structure 305$_{D3}$ corresponding to the tibia, by way of the corresponding mesh 306$_{D3}$ and associated texture 307$_{D3}$, as the synthesising of the specific description of the tibia 310$_{T3}$ begins, illustrated in FIG. 7B.

An embodiment of the software architecture comprises a local client application, which recognizes a user's voice request and then delivers the proper content; and a backend server receiving and answering remote application requests, storing special content and; providing a web interface for managing the special content.

The special content consists of sequences of pre-created screens combined with special parameters affecting screens representation on the client side, and cases embodying a combination of named text entity associated with aliases (tags), wherein the text of a case has one or more keywords and/or phrases associated with pre-created sequences.

In this embodiment, the workflow at the backend requires that medical problems or subjects that may be recognized and delivered as sequences 311$_N$, should be pre-created as cases using the web dashboard. A relevant number of screens including rendered 3D structures are created and stored at the server 103 into a special group. A relevant number of named sequences are then created, reflecting every aspect of every case that may be delivered. After that, cases are created by adding a new case entity, selecting keywords and key phrases inside the case text, and associating them with corresponding named sequences: every case should be equipped with aliases used for selecting a case upon speech recognition. A database of special content is thus gradually populated.

At the frontend, the application 303 starts and listens for user commands. It recognizes user's speech using the speech framework from the IOS® Software Development Kit ('SDK'). If words or phrases that are recognized, match aliases available in the database data, the corresponding case is selected at the server 103 and delivered to the IOS® application 303 as a sequence 311 to output. When the case reaches the client side at the user terminal 101, 102, the application 303 starts reading the case text by analysing this text and synthesizing the speech for the user can hear, using the AVFoundation framework from the IOS® SDK. During this process, when the processing encounters a keyword or key phrase, the application 303 starts playing the sequence associated with that keyword or key phrase. Thus, the user is listening to the machine-generated speech followed up by sequence screens illustrating what is being read, until the end of the case text. The user may then replay the case, or exit to initiate a new vocal request.

Accordingly, the techniques disclosed herein are particularly useful with medical reference software tasked with representing relationships between different anatomical structures and procedures, wherein the circumstances of the user, typically a medical practitioner, require hands-free interaction with the medical knowledge base in the course of a procedure or consultation.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

The invention is not limited to the embodiments hereinbefore described but may be varied in both construction and detail. For example, it will be readily understood by skilled persons that the inventive principle disclosed herein may be permanently integrated into the base configuration of an item through relevant manufacturing techniques, for instance injection moulding, rather than manufacturing the attachment device separately from the item to be secured thereto.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention claimed is:

1. A method of generating a digital audio-visual sequence comprising one or more three-dimensional structures and an audio stream in real time, comprising the steps of:
   a) capturing and processing vocal input from a user;
   b) identifying at least one semantic construct from the captured vocal input;
   c) matching identified semantic construct with at least one structure tag by applying a context identification algorithm comprising the steps of;
      i) comparing the identified semantic construct against a tree of structure tags;
      ii) identifying at least one structure tag that matches the identified semantic construct;
      iii) applying a confidence value to the identified at least one structure tag, the confidence value describing the degree to which the at least one structure tag matches the identified semantic construct;
      iv) where multiple structure tags are matched to the identified semantic contract, arranging the identified structure tags by confidence value; and
      v) selecting the structure tag having the highest confidence value relative to the other identified structure tags;
   d) matching identified semantic construct with at least one case tag;
   wherein the structure tag is associated with a three-dimensional structure and the case tag is associated with an alphanumerical description of the three-dimensional structure;
   e) generating a sequence based on one or more matched structure tag(s) and one or more matched case tag(s), wherein the step of generating further comprises
   f) scheduling synchronous rendering of the three-dimensional structure in a user interface and voice synthesising of the alphanumerical description.

2. A method of generating a digital audio-visual sequence as claimed in claim 1 wherein the tree of structure tags further comprises any from the group of at least a word index value, a command index value, a prefix length value, a value indicating the parent nodes and a value indicating the children nodes.

3. A method of generating a digital audio-visual sequence as claimed in claim 2 comprising the further steps of applying a best view algorithm, the best view algorithm comprising the steps of:
   a. formalizing the identified semantic construct as a set of terms for processing, the set of terms for processing;
   b. assigning formal properties to the set of terms;
   c. estimating the rendering of the three-dimensional structure using the assigned formal properties against a set of rules; d. generating a list of formal operations describing the steps required to render the three-dimensional structure;
   e. executing the list of formal operations.

4. A method of generating a digital audio-visual sequence as claimed in claim 1 comprising the further steps of applying a best view algorithm, the best view algorithm comprising the steps of:
   a. formalizing the identified semantic construct as a set of terms for processing, the set of terms for processing;
   b. assigning formal properties to the set of terms;
   c. estimating the rendering of the three-dimensional structure using the assigned formal properties against a set of rules; d. generating a list of formal operations describing the steps required to render the three-dimensional structure;
   e. executing the list of formal operations.

5. A method of generating a digital audio-visual sequence as claimed in claim 4 wherein the formal properties are selected from the group mathematical formal properties, contextual formal properties, and expert formal properties.

6. A method of generating a digital audio-visual sequence as claimed in claim 5 wherein the set of rules include any from the group of building context data, mathematical analysis of the three-dimensional structure, and expert formal properties analysis.

7. A method of generating a digital audio-visual sequence as claimed in claim 4 wherein the set of rules include any from the group of building context data, mathematical analysis of the three-dimensional structure, and expert formal properties analysis.

8. A method of generating a digital audio-visual sequence as claimed in claim 4 wherein the formal properties comprise contextual formal properties, wherein the contextual formal properties are determined by a set of contextual formal property rules.

9. A method of generating a digital audio-visual sequence as claimed in claim 6 wherein the contextual formal property rules are selected from the group all valid, only specified, all valid intermixed, and all valid except specified.

* * * * *